(12) United States Patent
Eifler et al.

(10) Patent No.: US 8,967,148 B2
(45) Date of Patent: Mar. 3, 2015

(54) RESPIRATORY DEVICE COMPRISING A FASTENING SYSTEM

(75) Inventors: Martin Eifler, Glückstadt (DE); Henry Hahn, Hamburg (DE); Joachim Gardein, Icod de los Vinos (ES); Anne Wonsyld, Hamburg (DE)

(73) Assignee: Weinmann Gerate fur Medizin GmbH & Co. KG, Hamburg (DE)

( * ) Notice: Subject to any disclaimer, the term of this patent is extended or adjusted under 35 U.S.C. 154(b) by 213 days.

(21) Appl. No.: 13/321,489

(22) PCT Filed: May 18, 2010

(86) PCT No.: PCT/DE2010/000584
§ 371 (c)(1),
(2), (4) Date: Dec. 5, 2011

(87) PCT Pub. No.: WO2010/133218
PCT Pub. Date: Nov. 25, 2010

(65) Prior Publication Data
US 2012/0111333 A1    May 10, 2012

(30) Foreign Application Priority Data
May 18, 2009   (DE) .......................... 10 2009 021 807

(51) Int. Cl.
*A61M 16/06* (2006.01)
*A62B 18/02* (2006.01)

(52) U.S. Cl.
CPC ....... *A61M 16/0683* (2013.01); *A61M 16/0633* (2014.02); *A61M 16/0638* (2014.02)
USPC ............ 128/206.21; 128/205.25; 128/206.28; 128/207.11

(58) Field of Classification Search
CPC ............... A61M 2016/0644; A61M 2016/065; A61M 2016/0655
USPC .......................... 128/203.29, 205.25, 206.12, 128/206.21–207.13
See application file for complete search history.

(56) References Cited

U.S. PATENT DOCUMENTS

| | | | |
|---|---|---|---|
| 2002/0020416 A1* | 2/2002 | Namey ...................... | 128/205.25 |
| 2006/0249157 A1* | 11/2006 | Eaton et al. .............. | 128/206.24 |
| 2007/0062537 A1 | 3/2007 | Chiesa et al. | |
| 2007/0240721 A1 | 10/2007 | Ho et al. | |
| 2008/0264422 A1* | 10/2008 | Fishman .................. | 128/207.11 |
| 2010/0071700 A2* | 3/2010 | Hitchcock et al. ........ | 128/207.11 |

FOREIGN PATENT DOCUMENTS

| | | |
|---|---|---|
| AU | 2007221773 | 4/2009 |
| DE | 10057893 | 7/2002 |
| EP | 1493461 | 1/2005 |
| EP | 2005987 | 12/2008 |
| WO | 2004021960 | 3/2004 |
| WO | 2007021777 | 2/2007 |
| WO | 2007143793 | 12/2007 |
| WO | 2008036625 | 3/2008 |

* cited by examiner

*Primary Examiner* — Valerie L Skorupa
(74) *Attorney, Agent, or Firm* — Abel Law Group, LLP

(57) ABSTRACT

The invention relates to a device for respiration which consists at least of one body that delimits an inner chamber from an outer chamber, a region for sealing the device against parts of the face of a patient, fastening elements for positioning the device on the patient's head and a connection for supplying respiratory gas. The device is equipped with an actuator, which when adjusted, changes the distance of at least one part of the device from at least one part of the body of the patient.

15 Claims, 18 Drawing Sheets

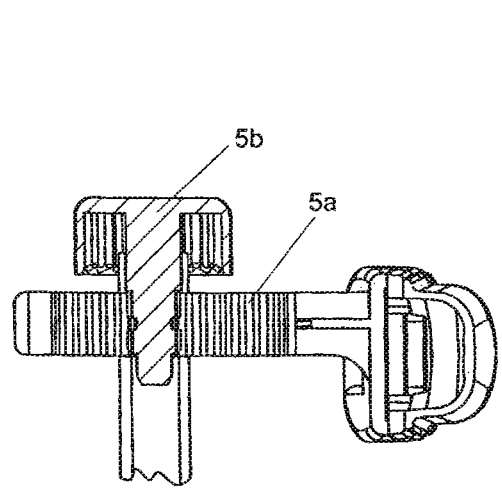
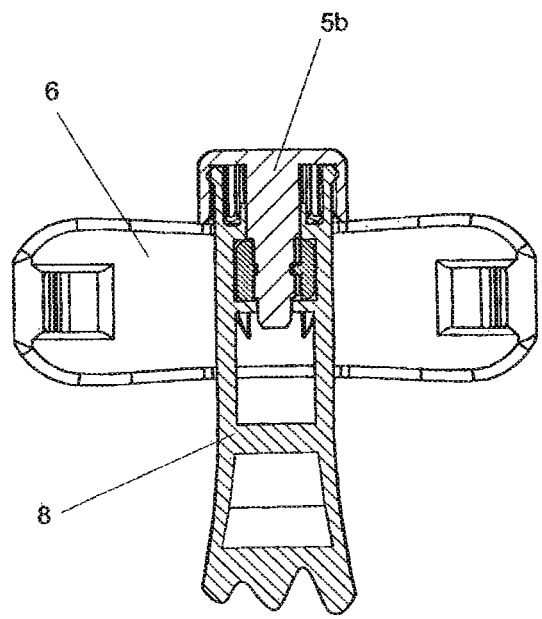
Fig. 1A
Fig. 1B
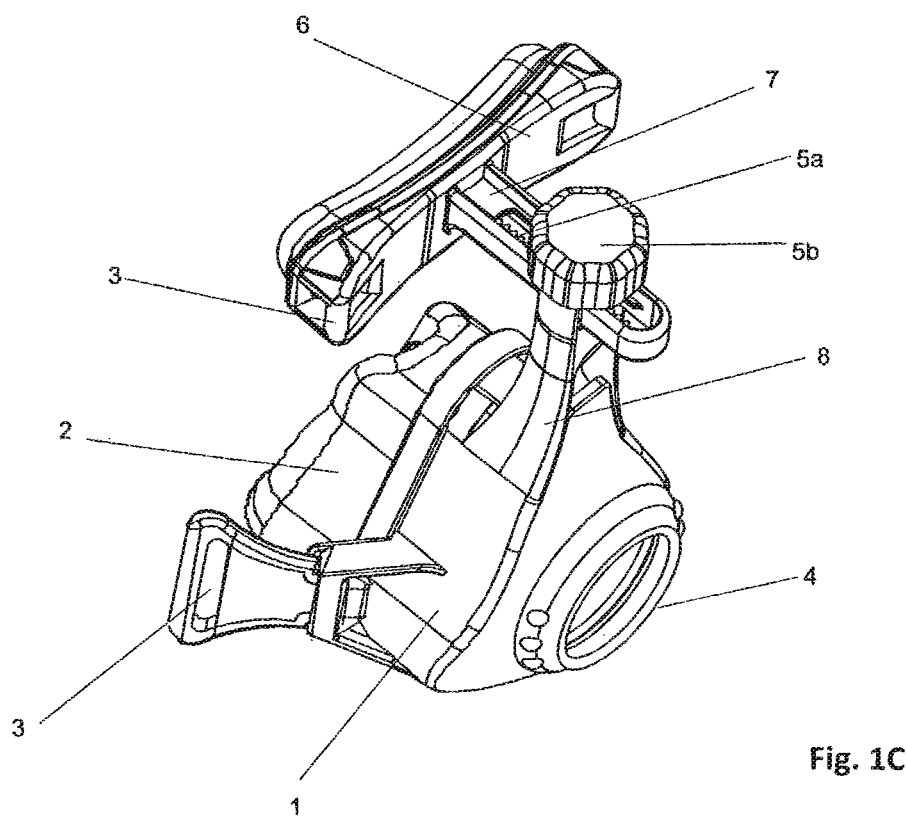
Fig. 1C

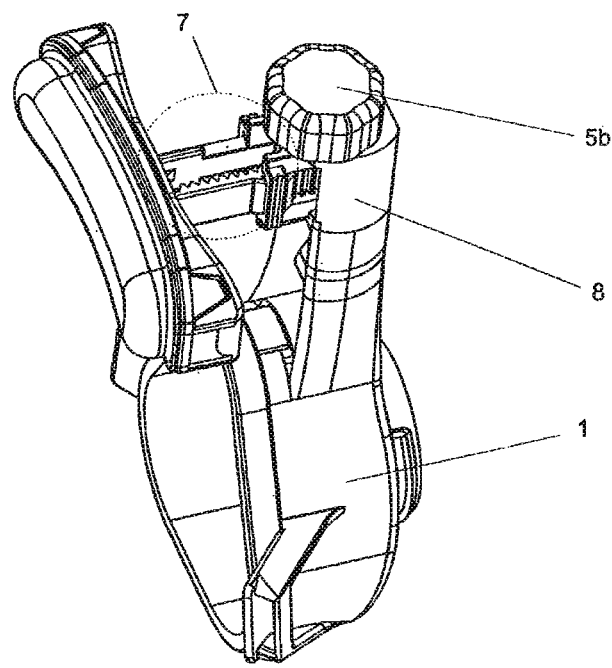
Fig. 2A
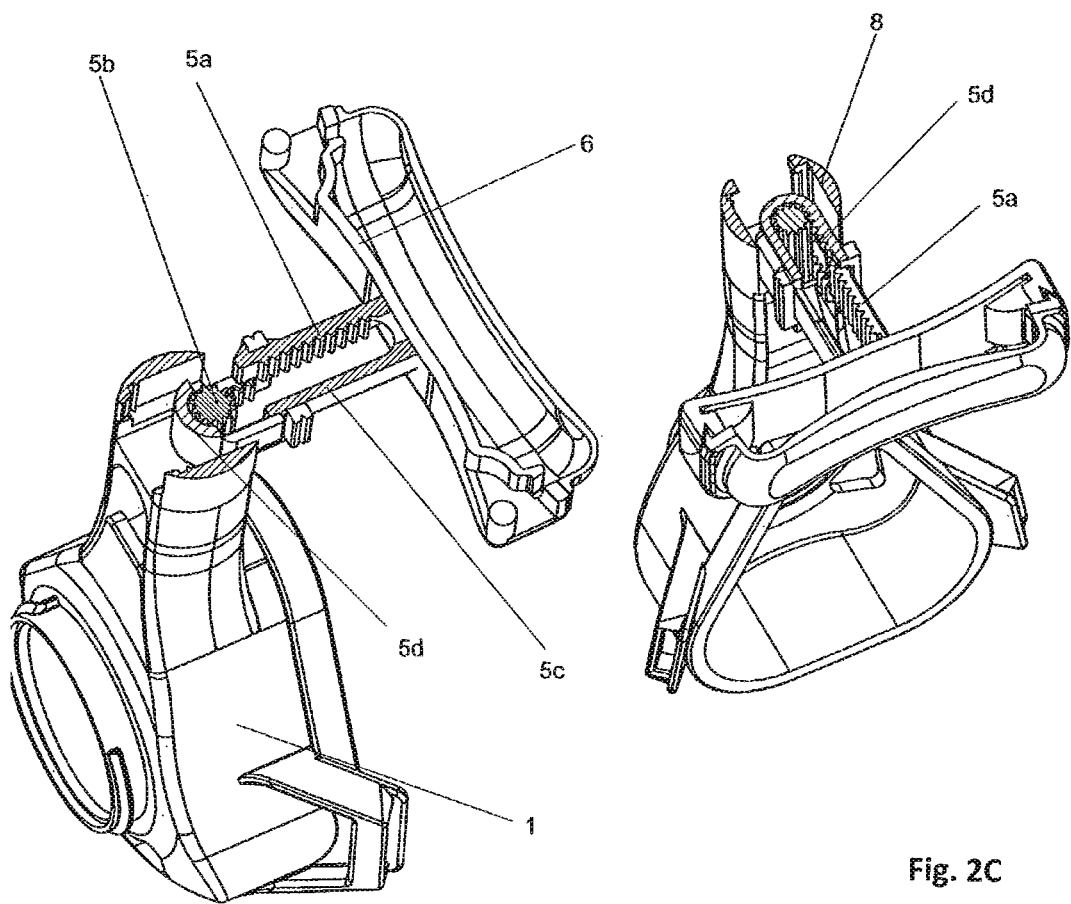
Fig. 2B
Fig. 2C

Detail X1

Detail X2

Detail X3

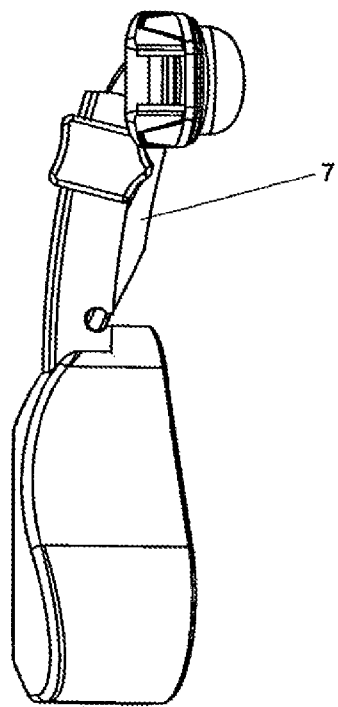
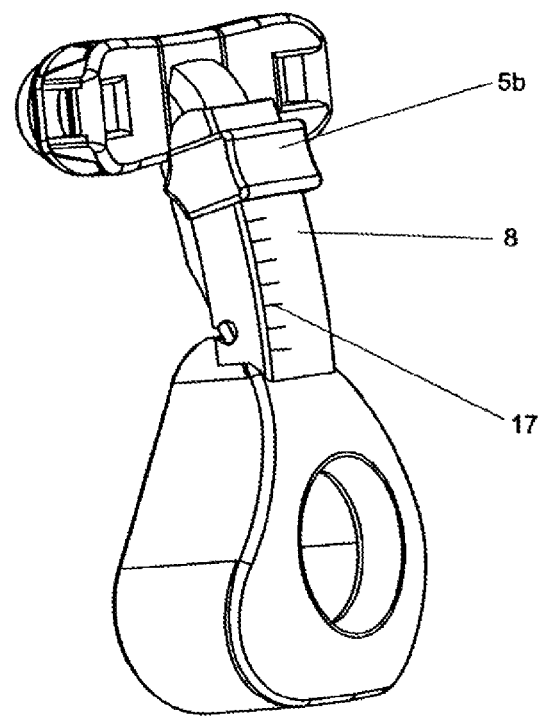
Fig. 9.1A    Fig. 9.1B
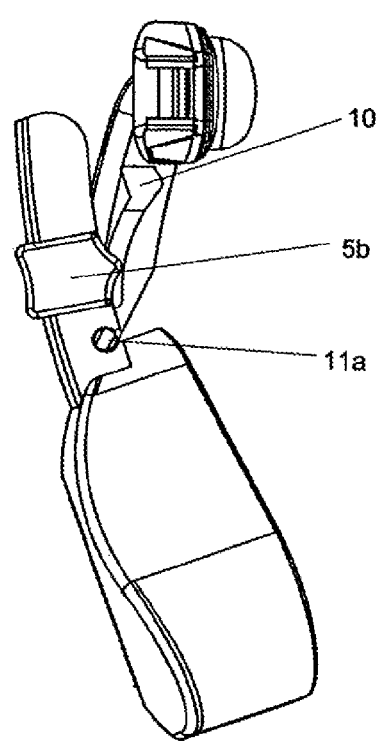
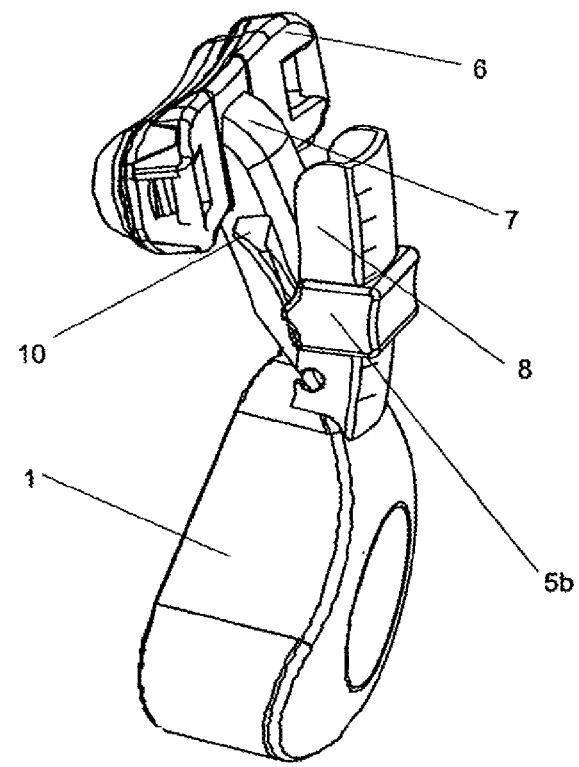
Fig. 9.1C    Fig. 9.1D

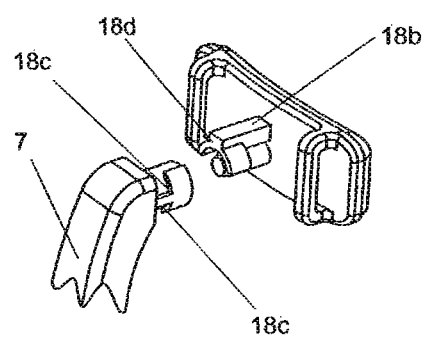
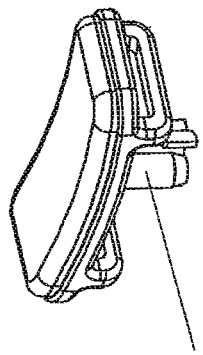
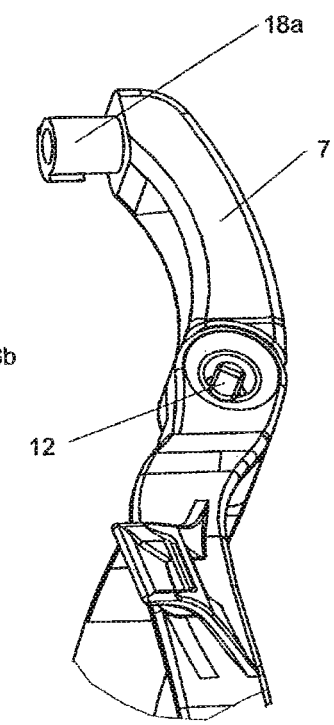
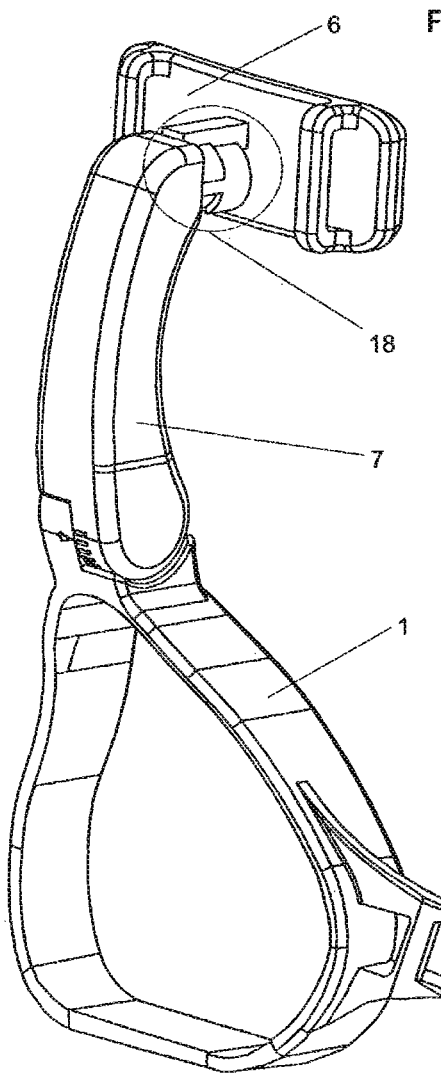
Fig. 12.1A
Fig. 12.1B
Fig. 12.1C
Fig. 12.1D

RESPIRATORY DEVICE COMPRISING A FASTENING SYSTEM

The invention relates to a breathing device with a fastening unit for fastening a patient interface to the head of the user.

The present application is a 371 of International application PCT/DE2010/000584 filed May 18, 2010, which claims priority of DE 10 2009 021 807.6, filed May 18, 2009, the priority of these applications is hereby claimed and these applications are incorporated herein by reference.

BACKGROUND OF THE INVENTION

Patient interfaces have the purpose of delivering breathing gas made available by a breathing apparatus to the patient. Patient interfaces can be realized in various embodiments, for example, as oxygen spectacles, pillow masks, nasal masks, or full face masks. The patient interface is typically connected to the breathing apparatus through a breathing gas hose and is secured to the head of the user.

A precise fit of the patient interface and of the fastening is required for avoiding therapy impairment, for example, due to slippage or separation.

For insuring a secure positioning of the breathing mask in the area of the face of the patient, and for reducing the forces acting on the face, breathing masks with forehead rests are used. Such interface rests typically have possibilities for vertical or spacing adjustments. However, many adjusting devices are often too complicated for the patient and can only be adjusted with difficulty by the patient or in sleep laboratories. A direct adjustment while wearing the mask is in most cases not possible.

By the additional use of a forehead rest at the patient interface which supplies the gas, for example, a nasal mask, the secure positioning of the breathing mask in the area of the face of a patient is ensured. An unintentional separation or slippage of the mask from the face of the user and any attendant leakages are avoided. The slippage of a poorly fitting patient interface may lead to unpleasant pressure points up to therapy impairments or therapy interruptions. The wearing comfort and the stability are increased by the use of a forehead rest. Pressure points in the contact area of the mask, which would occur in a breathing mask without forehead rest as a result of the pretension of the fastening straps, are avoided. However, for reducing the pressure acting on the bridge of the nose, an individual adjustment of the forehead rest relative to the mask is required.

SUMMARY OF THE INVENTION

Therefore, it is the object of the present invention to construct a breathing device of the type mentioned above in such a way that a functional, easy to operate adjustment of the forehead rest is made available and simultaneously a high functionality and robustness are provided.

In accordance with the invention, this object is met in that the breathing device has an adjusting member which when being adjusted changes a distance of at least one part of the device relative to at least one body area of the patient.

The change of the distance can be effected in different variations. All embodiments described in the following have in common that an operation can be effected which is simple to carry out by the patient, that a high robustness of the device is achieved and an unintentional adjustment can still be avoided.

BRIEF DESCRIPTION OF THE DRAWING

In the drawings, embodiments of the invention are illustrated schematically. The drawings show:

FIGS. 1A-1C, 2A-2C and 3A-3B (in the following collectively referred to as "FIG. 1", "FIG. 2" and "FIG. 3", respectively): Perspective views of masks with sectional detail views of the adjusting unit, FIGS. 4A-4D (in the following collectively referred to as "FIG. 4"): A perspective view of a mask with detailed views of the adjusting area.

DETAILED DESCRIPTION OF THE INVENTION

Figure 3A:
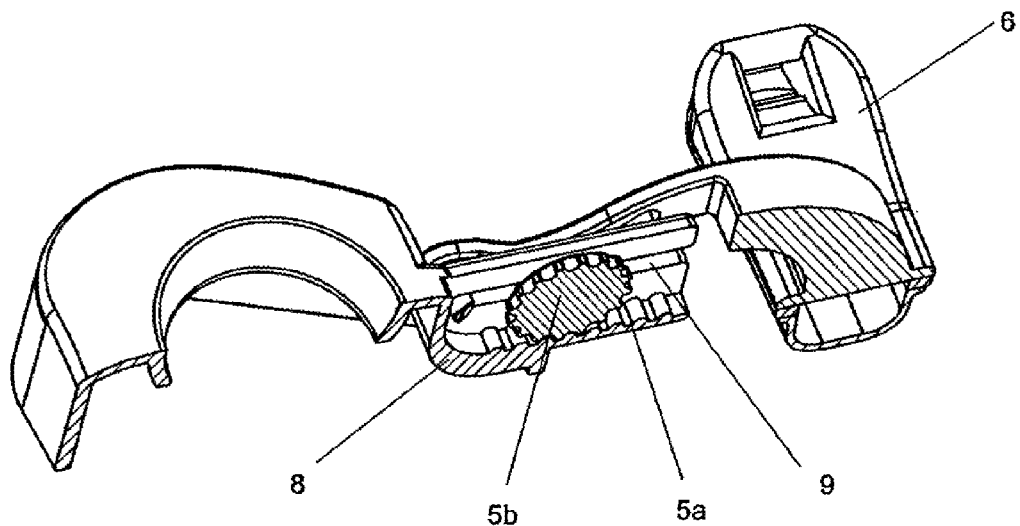

In an embodiment of the forehead rest adjustment (FIG. 1), the adjustment of the forehead rest 6 takes place through a rack 5a. The rack 5a is arranged in the arm 7 of the forehead rest support 6 and is constructed in such a way that it has a smooth surface on the outside and an oblong opening on the inside, similar to a groove with small teeth at a side thereof. An opening for receiving the arm of the forehead rest support 7 is located in the shaft of the forehead rest 8 which is integrated with the mask body 1. The arm of the forehead rest support 7 is inserted into the opening and can move back and forth in the opening. Through a further opening in the forehead rest shaft 8, the adjusting unit 5b, which has on the axis a small gear wheel, is passed through the rack 5a and is locked in the shaft of the forehead rest 8. By turning the adjusting unit 5b, the gear wheel moves in the rack 5a and adjusts the forehead rest 6 back and forth relative to the mask body 1. The arm of the forehead rest support 7 can be removed by an easy disassembly of the adjusting unit. This arm is arranged asymmetrically with respect to height on the forehead rest support 6 and offers a simple height adjustment of the forehead rest by turning the forehead rest support 6 180°. Handling is simple and is composed only of a few simple parts. The forehead rest is secured to the head of the patient through commercially available head straps or hoods which are fastened to the sides of the forehead rest support 3.

In a slightly modified embodiment of the rack adjustment (FIG. 2), an open toothed rail 5a is mounted on the forehead rest support 6 instead of the one-piece arm, and another smooth rail 5c is mounted for guidance. They are arranged on the forehead rest support 6 asymmetrically with respect to height and outside the middle. The toothed rail forms the first adjusting part of the rack adjustment. A U-shaped second toothed part 5d forms together with the toothed rail 5a and the rail 5c the arm of the forehead rest support which can be moved in or apart telescopically. Provided in the second toothed part 5d is a receiving means for the guide rail 5c and an opening into which the first toothed rail 5a is inserted. The outer side of the first toothed rail 5a has a locking nose which engages in the opening of the second toothed part 5d. Both parts together are placed in the opening of the forehead rest shaft 8 and, through another opening in the forehead rest shaft 8, the adjusting unit 5b, which has a toothing on the axis, is guided from the outside through the rack 5d and is locked in the shaft of the forehead rest 8. By rotating the adjusting unit 5b, the toothed axis of the adjusting unit 5b moves in two-part rack and in this manner adjusts the forehead rest 6 back and forth relative to the mask body 1. This is functioning telescopically in two stages. First, upon rotating the adjusting element 5b only the first toothed rail part 5a moves and, only when the locking nose of the first toothed part 5a rests against the stop of the opening of the second toothed part 5d, the first toothed part 5a takes along the second toothed part 5d. The first toothed part 5a fits telescopically into the second toothed part 5d. Because the toothed parts slide telescopically into each other, the arm of the forehead rest support 7 has a very small structural size.

Figure 3B:
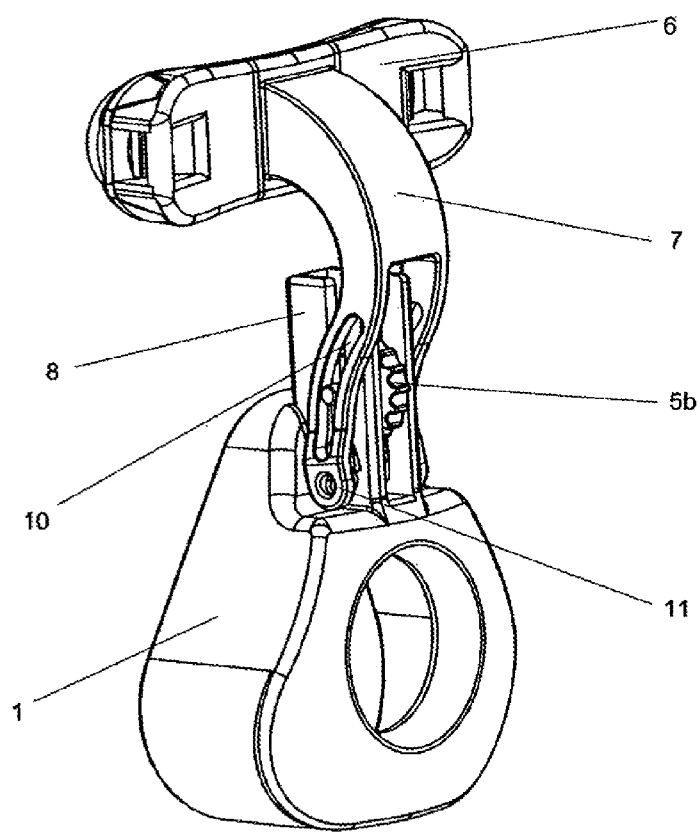
Figure 4A:
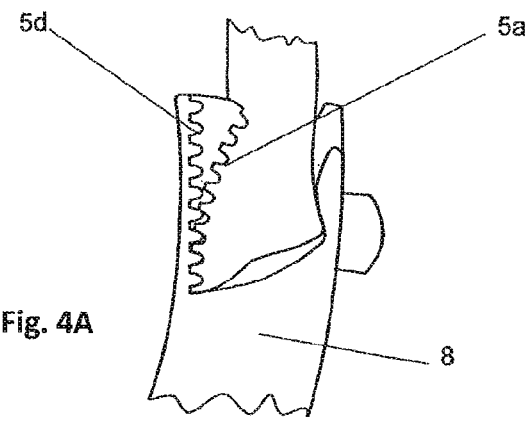
Figure 4B:
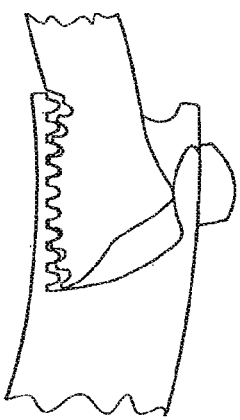
Figure 4C:
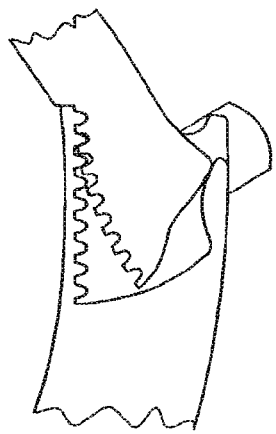
Figure 4D:
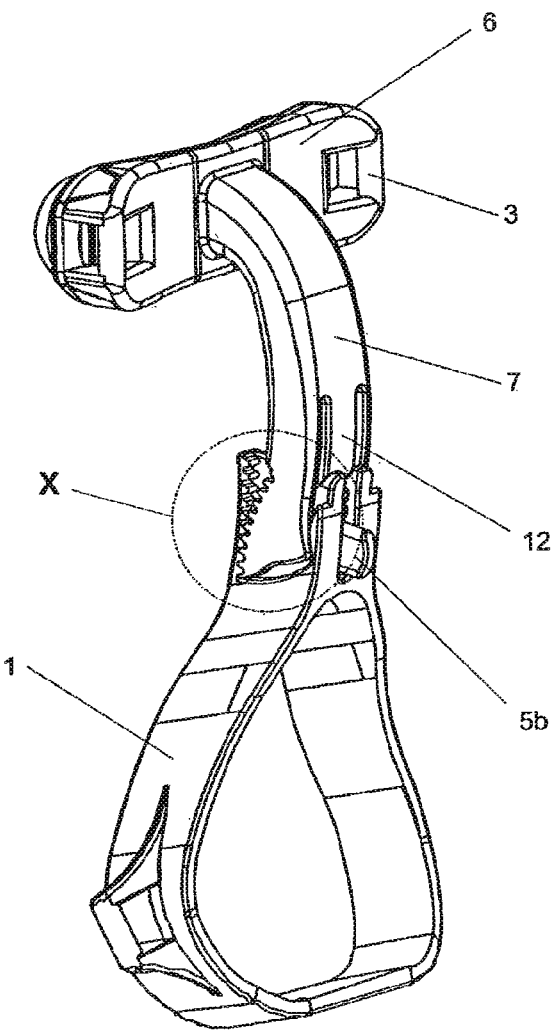

A further embodiment of the rack adjustment (FIG. 3) is realized by a toothed running surface 5a in the interior area of the forehead rest shaft 8. The forehead rest shaft 8, which is integrated into the mask body 1, is hollow and open toward the front, has in its interior a toothed running surface 5a and has slots on the side. These slots 9 serve for guiding a gear wheel 5b. The gear wheel 5b serves for adjusting the forehead rest 5b. It is constructed in such a way that it has axes on both sides which extend in the slots 9 of the forehead rest shaft 8 and simultaneously in the curved grooves 10 laterally in the arm of the forehead rest support 7. The arm of the forehead rest support 7 is curved in S-shape in the side view, is slotted in the lower area thereof and has locking means at the ends of both sides which engage in corresponding openings in the forehead rest shaft 8. By rotating the gear wheel 5b, the forehead rest 6 is adjusted back and forth relative to the mask body 1 about the locking point 11 in the forehead rest shaft 8. The virtual axis of the gear wheel carries out a stretched movement and, because of the shape of the forehead rest support 7, effects an adjustment in the direction of the forehead of the patient.

Stretched movements are to be understood to be movements which occur linearly or in a large arc. The arc may be a circular path or a chosen path. A stretched movement is present particularly when the radius of the movement of at least one point of the adjusting member is greater than about 25 mm at least on a partial segment of the movement path. In a preferred embodiment, the radius of the movement of at least one point of the adjusting member on at least a partial segment of the movement path is greater than about 50 mm. Especially preferred is a radius of the movement of at least one point of the adjusting member on at least a partial segment of the movement path greater than about 75 mm.

A stretched movement is also present if the movement of the adjusting member constitutes a superposition of several movement forms. Thus, rolling of a toothed wheel on a linear or curved contour of a rotation about the (possibly virtual and moveable with respect to location) gear wheel axis, with simultaneous displacement of the gear wheel along the path of the rolling partners. In that case, the (possibly virtual and moveable with respect to location) axis of the gear wheel can carry out a stretched movement in the sense of the above-described definition. A (possibly virtual or moveable with respect to location) axis is a part of the adjusting member and, consequently, can carry out a stretched movement in the sense of the above-described definition.

Furthermore, a stretched movement is present if a point of the adjusting member carries out a stretched movement in the sense of the above-described definition, while the adjusting member itself can carry out any chosen complex movement.

In preferred embodiments, the movement of the adjusting element does not take place proportionally to the movement carried out by the forehead rest. This takes place at least in partial areas of the adjusting path and can be applied to all embodiments described herein.

Due to the non-proportional transmission of the movement, a finer adjustment is made possible, for example, in the middle adjusting range than in the outer adjusting ranges.

FIG. 4: In a further embodiment variation with a toothed adjusting possibility of the forehead rest 6, this is made possible by rolling of the forehead rest 6 on curved toothings 5a at the slotted arm of the forehead rest support 7 on the respective toothed surface 5d on the outside of the forehead rest shaft 8. Also possible would be the rolling on a smooth surface. Rolling over a toothed surface serves for a better guidance. The arm of the forehead rest support 7 is divided; it has a resilient element 12 with an adjusting knob 5b and lateral rolling surfaces 5a. The rolling movement is fixed or blocked by means of a second geometry (illustrated in the detail views X1 to X3). The resilient element 12 has locking noses which block the rolling movement by engaging in various grooves in the forehead rest shaft 8 and thereby fix the forehead rest 6 in the desired position. This does not constitute a linear forward and rearward positioning of the forehead rest 6, but rather a simultaneous adjustment of the height and the distance of the forehead rest 6 relative to the head of the patient, which is not shaped circular but approximately like an evolvant. This is due to the fact that no fixed axis of rotation has been predetermined.

As an alternative to the adjustment of the forehead rest through toothed adjusting possibilities, it is apparent that the forehead rest shaft can be divided into several elements and to adjust these elements by displacing at least one of the elements on an inclined plane. The adjustment is variably positionable on the inclined plane and is in this manner adjustable for the user to his/her individual face topography. The particular advantage for the user is the simultaneous height as well as depth changes of the forehead rest. Thus, all anatomic features such as, for example, bulges over the eye and also topographic differences based on ethnicity can be compensated. Embodiments are described in the following figures.

Figure 5:
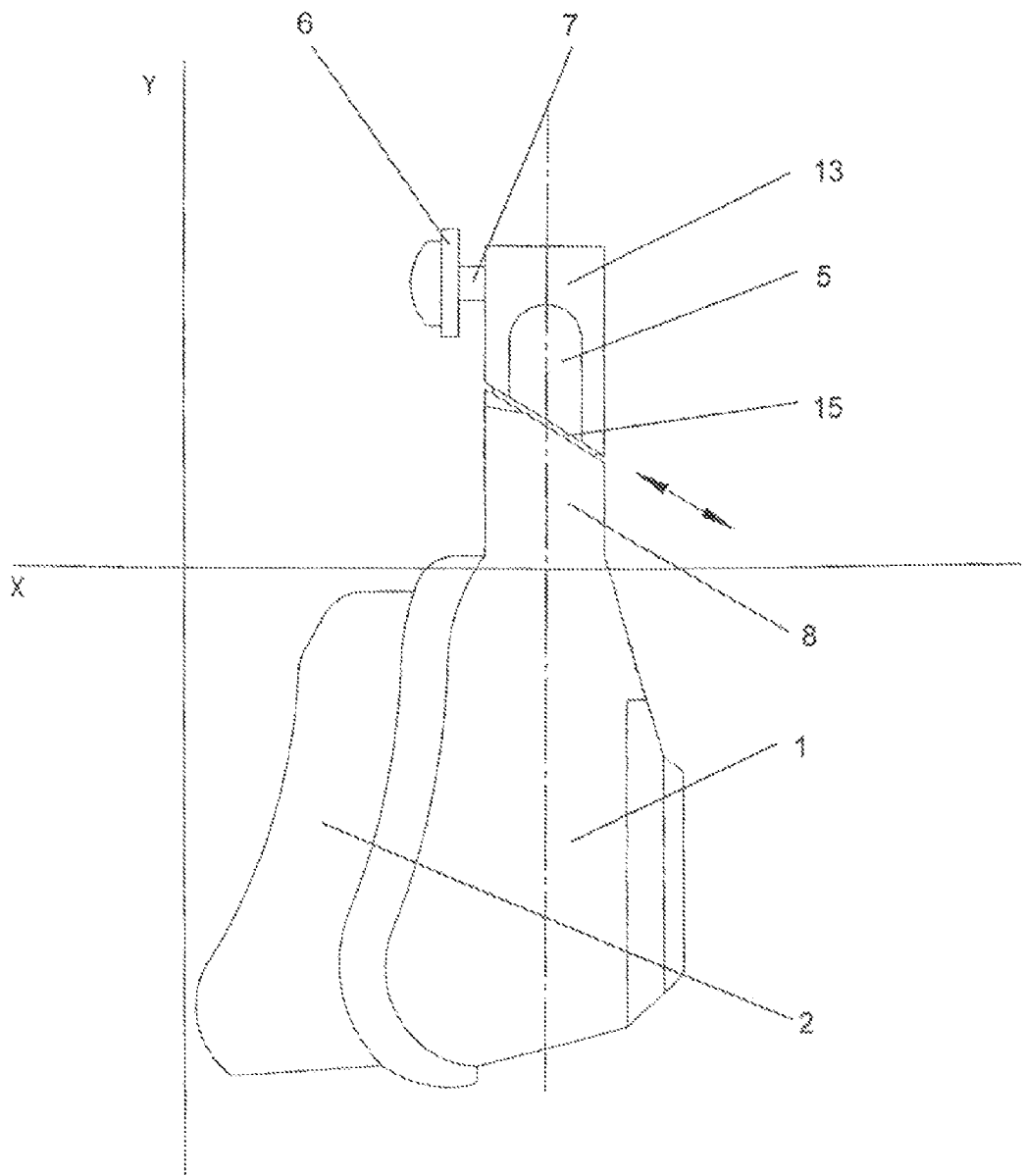
FIGS. 5 to 8: Schematic illustrations of masks with adjusting possibilities through inclined planes, FIGS. 9A-9D (in the following collectively referred to as "FIG. 9"): Perspective views of a mask in two adjusting areas with longitudinal sectional views, FIGS. 9.1A-9.1D (in the following collectively referred to as "FIG. 9.1"): Perspective and side views of a mask.

The forehead rest of FIG. 5 is composed of at least two adjusting elements which are moveable relative to each other. The forehead rest shaft 8 is connected to the PI supplying the gas in the area of the mask body 1 and forms the first adjusting element. The second adjusting element 13 is connected through the arm 7 to the forehead rest 6. At least one of the elements has possibilities for securing to the head, for example, through eyes or clips for receiving straps or a hood.

The surfaces of the two adjusting elements, which are placed on top of each other, extend parallel relative to each other and have an angle of between 1° and 89° relative to the X-axis, so that an inclined plane 15, respectively, is created. Along this plane 15, the elements 8, 13 are displaceable and lockable relative to each other in at least two variable positions. When the second element 13 is moved, the distance of the forehead rest 6 to the X-axis changes in such a way that the forehead rest 6 is moved back and forth parallel to the Y-axis. Simultaneously, the second adjusting element 13 is adjusted with respect to height relative to the Y-axis. As long as the user applies a slight pressure against the arched surfaces 5 of the adjusting element, the forehead rest shaft 8 and the adjusting element 13 can be moved relative to each other along the sliding surfaces 15. On at least one of the end points of the sliding surfaces of the adjusting part 13 and/or the forehead rest shaft 8, a stop for locking is arranged, so that the parts cannot slide apart in their entirety.

Figure 6:
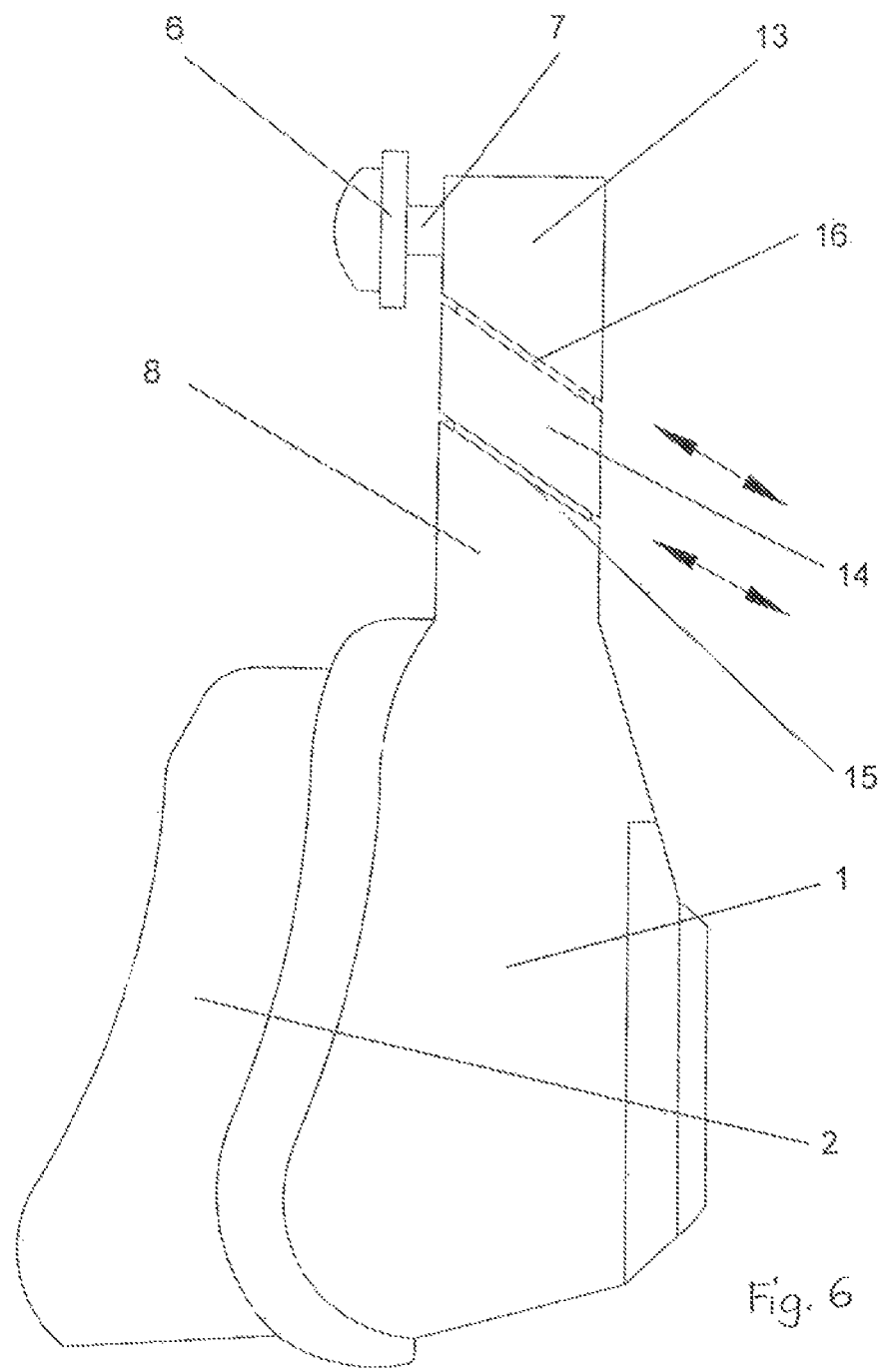
Figure 7:
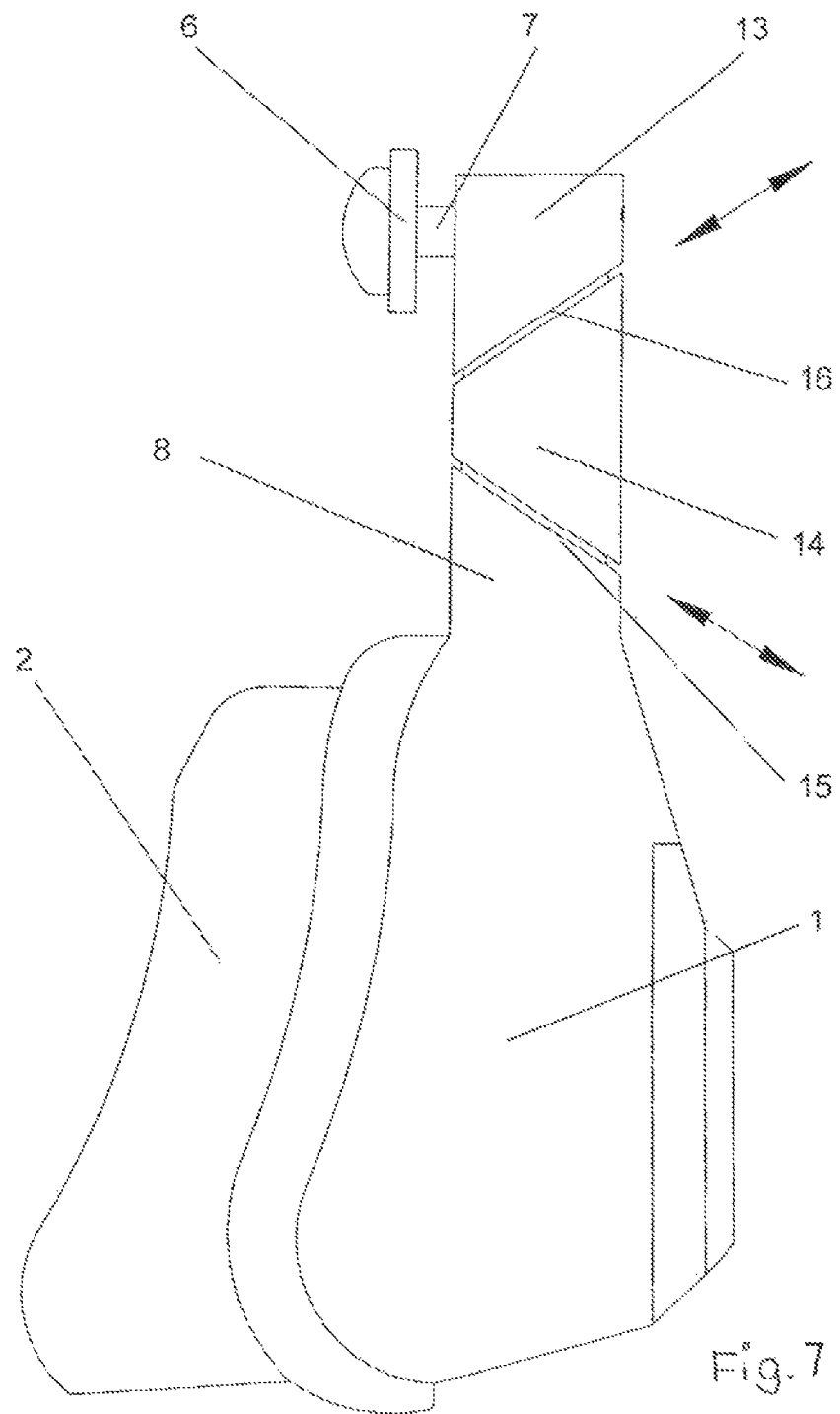
Figure 8:
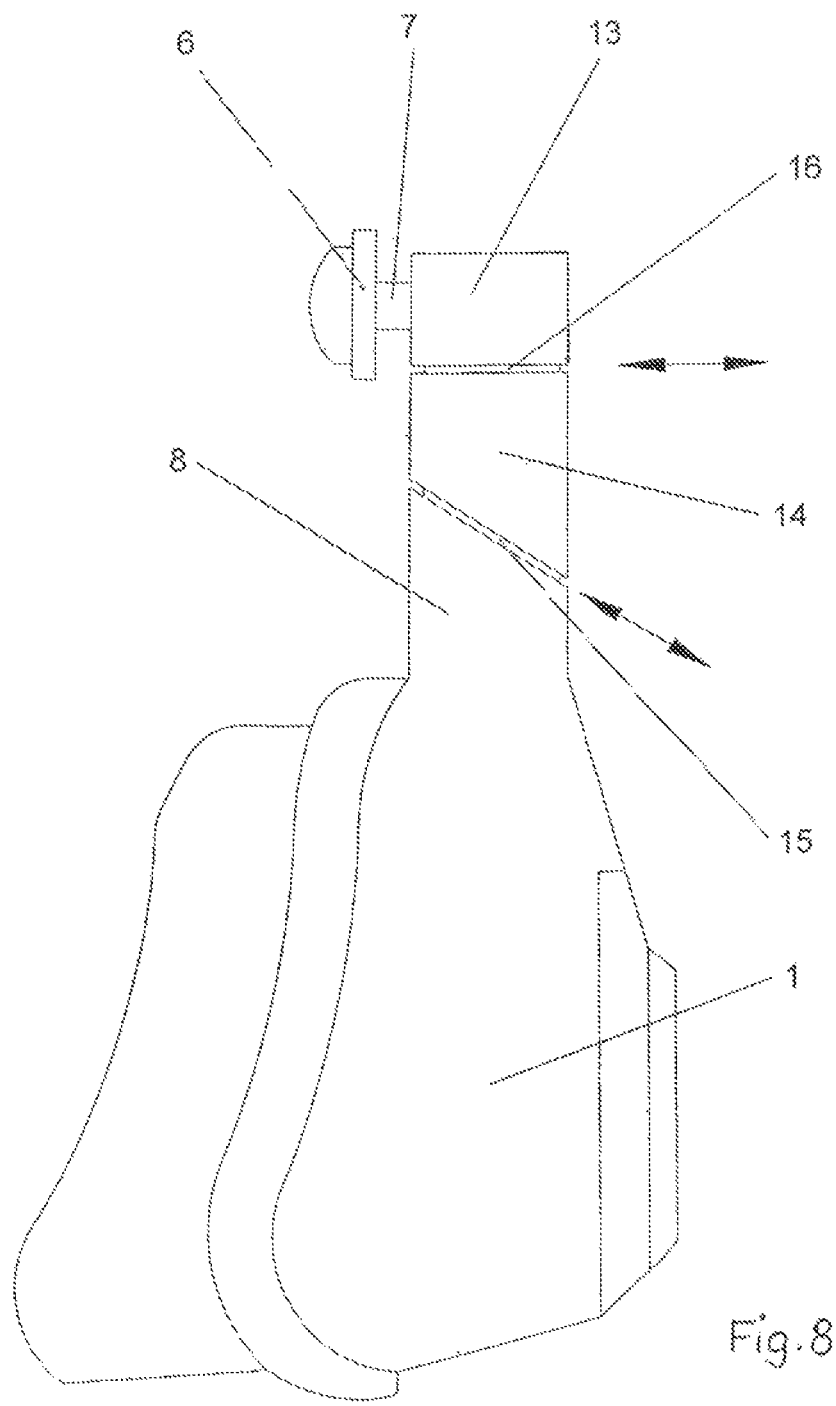

The breathing masks with forehead rest according to FIG. 6, FIG. 7 and FIG. 8, are composed of at least three elements which are arranged so as to be slidable against each other/with each other. The forehead rest shaft 8 is connected to the gas-supplying PI in the area of the mask body 1 and the adjusting element 13 is connected to the forehead rest support 6 through the arm 7. Arranged therebetween is another third adjusting element 14. The adjusting element 14 can be moved over two sliding surfaces 15, 16. The additional adjusting element 14 provides a larger adjusting area. In FIG. 6, the two sliding surfaces 15, 16 are arranged parallel to each other. This makes it possible to achieve a larger adjusting area with respect to height, i.e., in the direction of the X-axis. FIG. 7, on the other hand, shows an opposite but equal arrangement of the sliding surfaces 15, 16. This makes it possible to achieve a greater adjusting range in the depth, i.e., in the direction of the Y-axis. Another possibility of arranging the sliding surfaces 15, 16 is illustrated in FIG. 8. This embodiment would be advantageous, for example, for face contours having a low forehead height, but with a forehead which juts out toward the front to a significant extent.

In accordance with the invention, the embodiments of FIGS. 5 to 8 can also have smooth sliding surfaces which facilitate a gradual adjustment without locking. In that case, fixing in a position is effected by clamping.

Figures 9A, 9B:
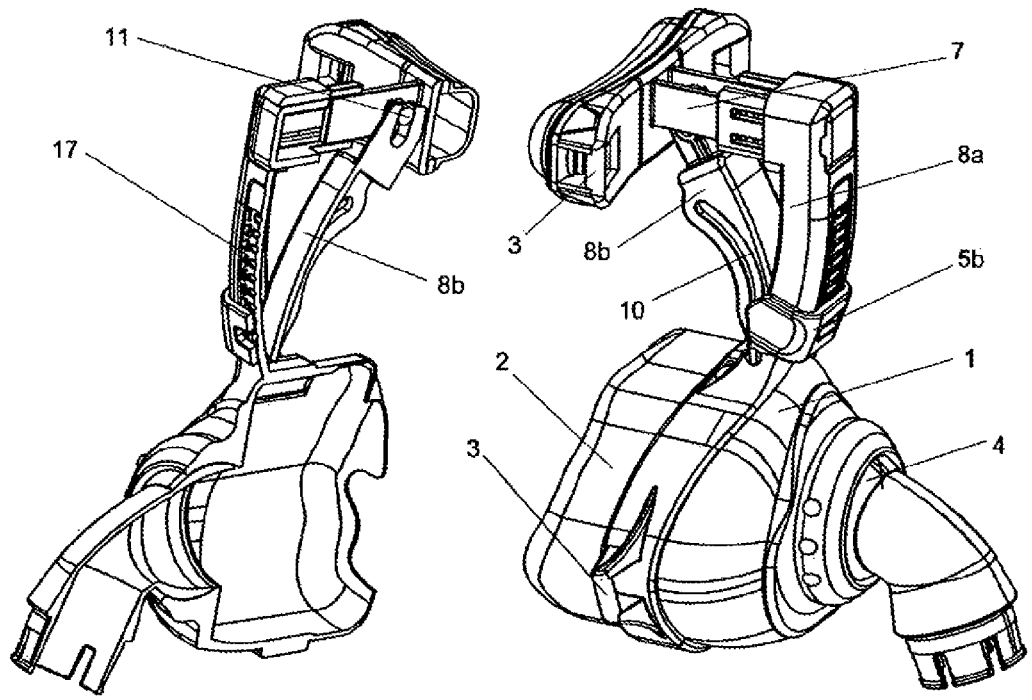
Figures 9C, 9D:
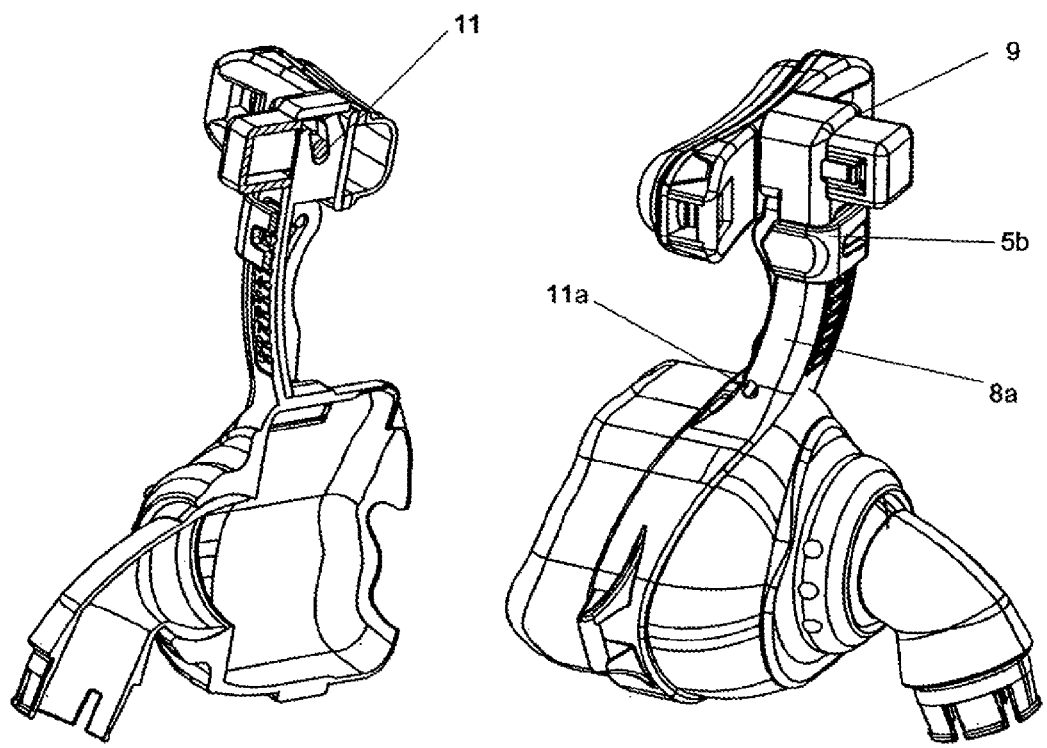

FIG. 9 shows another alternative embodiment of the forehead rest adjustment. In this forehead rest adjustment, the forehead rest shaft 8 is composed of two parts, a stationary part 8a, connected to the mask body 1, and a movable part 8b. The stationary part 8a of the forehead rest shaft has an opening 9 in which the arm of the forehead rest 7 is received. The arm of the forehead rest support 7 is composed of parts which can be moved telescopically into each other. The movable part of the forehead rest shaft 8b is connected at the upper end through a snap-type connection 11, to an axis of the forehead rest support, to the telescopic arm of the forehead rest support 7. The lower end of the movable forehead rest shaft 8b is connected rotatably through two holding elements (pins) 11a to the stationary part 8a and is constructed in such a way that it can fit into the stationary part 8a. Moreover, the movable part 8b of the forehead rest shaft has guide grooves 10 in which guide elements (pins) of a slide member 5b engage. The slide member 5b serves as an adjusting element and moves on the contour of the stationary part 8a of the forehead rest shaft in a stretched movement. Moreover, the slide element serves as an adjusting element and moves on the contour of the stationary part 8a of the forehead rest shaft in a stretched movement. By moving the adjusting element (slide member) 5b, the movable part 8b of the forehead rest shaft in the stationary part 8a is moved and takes along with it the telescopic arm of the forehead rest support 7. The forehead rest 6 is horizontally linearly moved back and forth as a result.

Preferred is a mechanical actuation of the telescope, however, a hydraulic, pneumatic, etc. actuation is possible.

A somewhat simpler alternative embodiment of the forehead rest adjustment is illustrated in FIG. 9.1. In that case, a forehead rest adjustment is used composed of two parts which include a forehead rest shaft 8 which is fixedly connected to the mask body 1 and a movable forehead rest support arm 7 which moves in the forehead shaft 8 when the forehead rest 6 is adjusted. The connection between the forehead rest shaft 8 and the forehead rest support arm 7 takes place through two holding elements (pins) 11a which are arranged on the forehead rest support arm 7 and are rotatably supported in the forehead rest shaft 8. The forehead rest support arm 7 is narrower than the shaft 8 and moves back and forth in the shaft.

The adjustment takes place through the movement in a stretched movement of a slide member 5b which engages through the stationary forehead rest shaft 8 and includes guide elements (pins) which engage in guide grooves 10 in the forehead rest support arm 7 and move the latter during adjustments.

The guide grooves 10 in the forehead rest support arm 7 extend upwardly slightly inclined and, by applying a slight pressure on the slide member 5b, cause spreading of the slide member 5b which can then be easily disassembled. Consequently, the support elements 11a of the movable forehead rest support arm 7 can be removed from its lower support.

For the assembly, the holding elements 11a of the forehead rest support arm 7 are clicked into the counter bearings in the forehead rest shaft 8, the slide member 5b can then be easily inserted from above into the guide grooves 10, or the guide elements (pins) of the slide member 5b can expand as a result of a pivoting movement of the forehead rest support arm 7 and snap back again into the guide grooves 10.

In accordance with the invention, it is also being considered to provide a marking 17 of the adjusted position of the support element 6 or of the adjusting member 5b. For example, a special adjusted position, and adjusting range or a middle position of the adjusting range can be marked, as well as all locked positions. This can be effected by an optical and/or acoustic and/or tactile marking 17 of the adjusted position of the support element or the adjusting member. It is also possible to have several positions or position ranges within the adjusting range of the support device.

Figure 10:
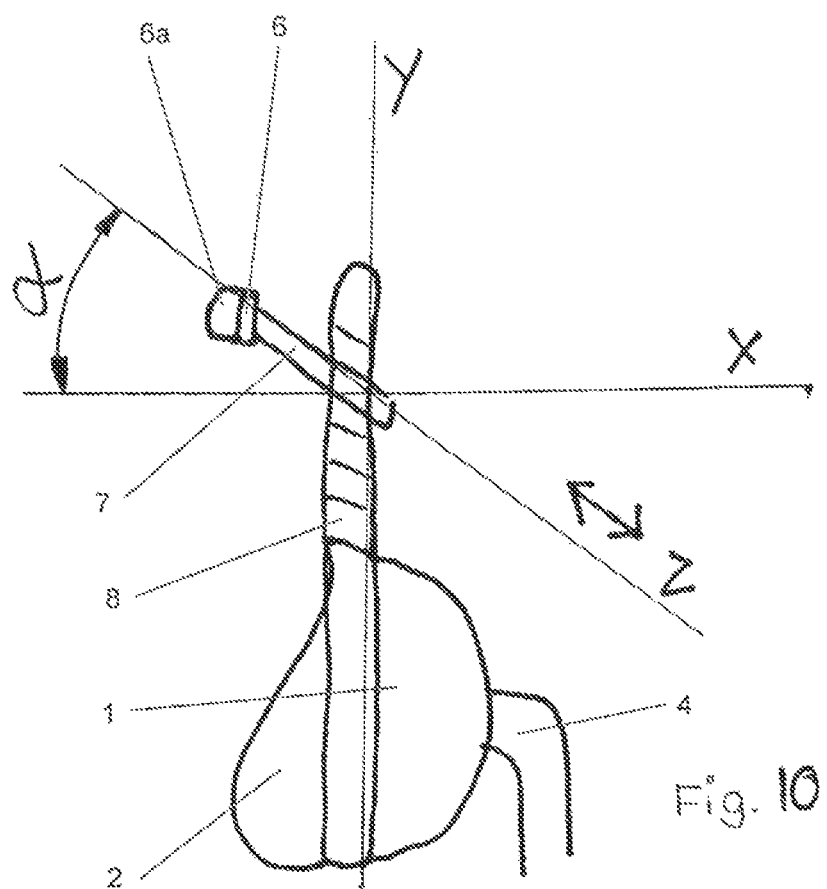
FIGS. 10, 11: Schematic illustrations of a mask with adjusting possibilities vertically or at a specified angle alpha, FIGS. 12A-12D (in the following collectively referred to as "FIG. 12"): Side views of a mask in two adjusting areas and exploded views of the individual parts of the forehead rest adjustment, FIGS. 12.1A-12.1D (in the following collectively referred to as "FIG. 12.1"): A perspective illustration of a forehead rest adjustment and exploded views of the bayonet connection, FIGS. 13A-13D (in the following collectively referred to as "FIG. 13"): Views of a forehead rest support with adjusting device, FIGS. 14A-14B (in the following collectively referred to as "FIG. 14"): A perspective illustration of a mask with overhead support pad and detail of the adjustment, FIGS. 15A-15B (in the following collectively referred to as "FIG. 15"): A perspective and exploded view of a clamp connection, and FIGS. 16A-16B (in the following collectively referred to as "FIG. 16"): A perspective side view and internal view of a clamping device.

FIG. 10 shows the adjustment of the forehead rest 6 in which the forehead rest shaft 8 extends perpendicularly of the X-axis, here shown as Y-axis, and the forehead rest support 6 includes with the forehead support pad 6a a fixed angle alpha relative to the X-axis in the direction of the illustrated Z-axis. The angle alpha may be between 1° and 89° relative to the X-axis. The forehead rest support 6 is variably slidable and lockable along the Z-axis. The angle between the forehead rest shaft 8 and the forehead rest support 6 with the forehead support pad 6a remains constant. When displacing the forehead rest support 6 along the Z-axis relative to the forehead shaft 8, the distance of the forehead support pad 6a relative to the X-axis changes in such a way that the latter is slidingly moved back and forth parallel to the Y-axis. A predetermined pattern in the forehead rest shaft 8 facilitates a change of the height of the forehead rest support 6 along the Y-axis.

Figure 11:
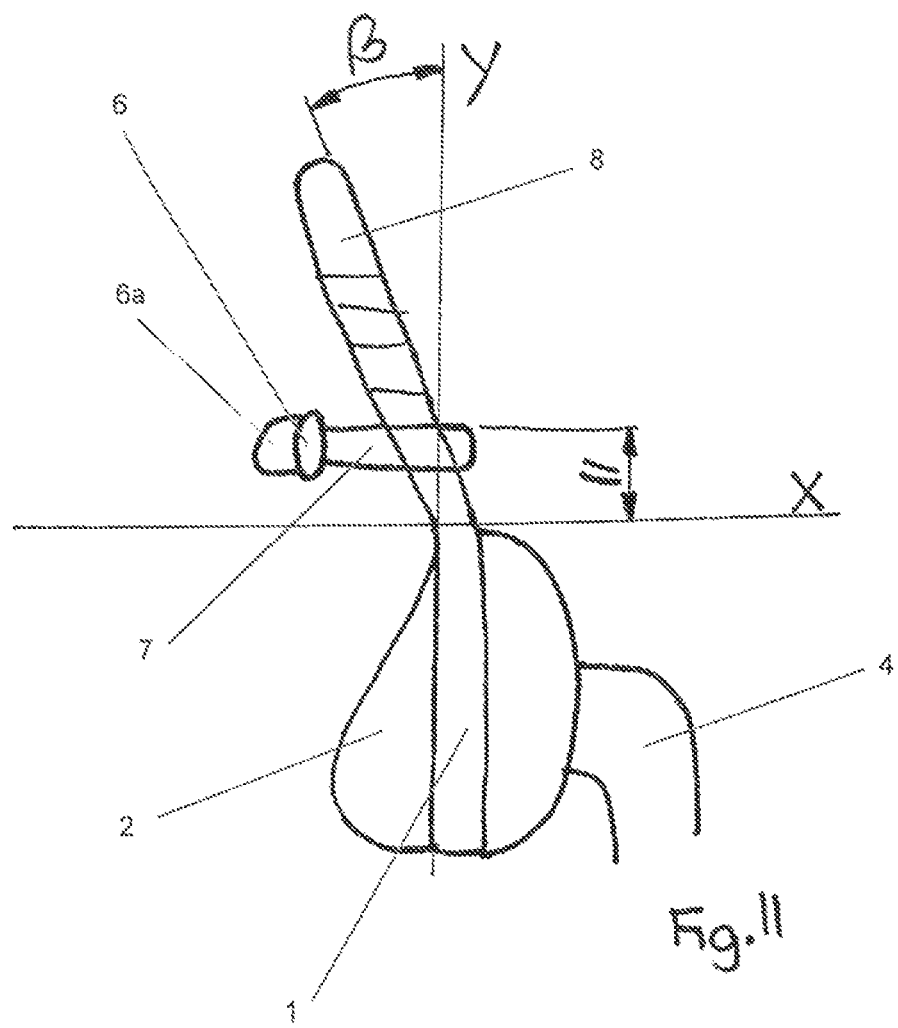

The forehead rest shaft 8 cannot only be perpendicular to the Y-axis but rather, as illustrated in FIG. 11 may have a slightly curved shape toward the face of the patient. The forehead rest support 6 moves in the case of the adjustment linearly along the curve. In the vertical pattern which is also predetermined in the forehead rest shaft 8, an even larger adjusting range is created. It is also possible to design the forehead support shaft 8 at a fixed angle beta relative to the Y-axis. In that case, the forehead rest support 6 is arranged parallel to the Y-axis. The angle between the forehead rest shaft 8 and the forehead rest support 6 with the forehead support pad 6a remains constant during the adjustment.

The adjustment of the forehead support pad 6a as described above, can be effected by displacing and locking the forehead rest support 6 in the forehead rest shaft 8 or through threaded parts which serve for adjusting. In that case, all forehead rest parts, the shaft 8, the arm of the forehead rest support 7 and the forehead rest 6 have threaded parts. The rotation of the threaded parts makes it possible to select a position of the forehead support pads 6a and the locking means thereof which are suitable for the patient.

Figures 12A, 12B:
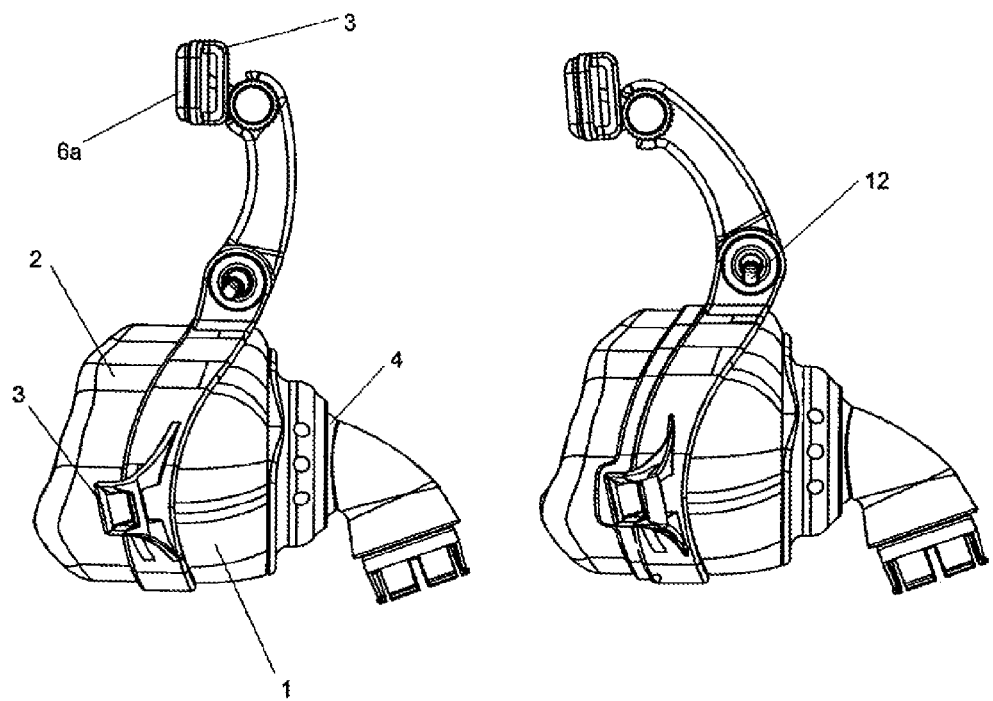
Figures 12C, 12D:
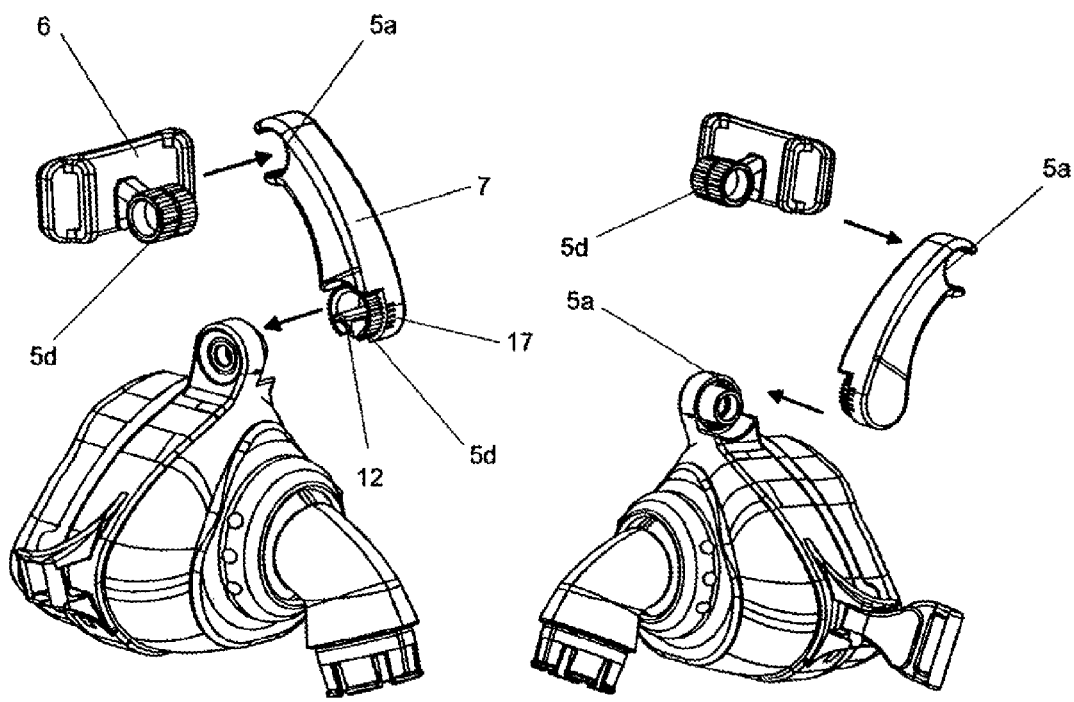

FIG. 12: Another alternative adjustment of the forehead rest 6 is facilitated by an embodiment variation whose adjustment is only possible in the horizontally uncoupled state. A circular ring-shaped receiving means 5a having internal teeth, similar to a toothed wheel which can receive an externally toothed counterpiece 5d arranged at the lower end of the forehead rest arm 7 and in this manner form a unit which belongs together.

For changing the position of the forehead rest 6 this connection is separated by applying a slight pressure to a snap hook 12 at the forehead rest arm 7. These two elements, i.e., mask body 1 and forehead rest arm 7 are subsequently mounted again in a changed position relative to each other. Provided at the upper end of the forehead rest arm 7 is also an inwardly toothed receiving means 5a which has an opening in the direction of the forehead rest 6, and an externally toothed counterpiece 5d provided at the forehead rest 6. The latter serves for adapting the forehead rest 6 to the forehead support pad 6a to the relatively changed position of the forehead rest arm 7. For this purpose, the forehead rest 6 is pulled horizontally out of the receiving means 5a and is once again mounted in a changed position. The outwardly toothed element 5d at the forehead rest 6 is arranged vertically outside of the middle and thereby facilitates a vertical adjustment by turning by 180°.

An alternative height adjustment of the forehead rest 6 is illustrated in FIG. 12.1. The connection of forehead rest arm 7 and forehead rest 6 is similar to a bayonet closure 18. A cylindrical receiving means 18a is mounted at the forehead rest arm 7. The cylindrical receiving means 18a has a laterally undercut stop 18c. The forehead rest 6 has a cylindrical counterpiece 18b which fits into the cylindrical receiving means 18a of the forehead rest arm 7, and a semicircular stop area 18d which is guided in the vertical position of the forehead rest 6 over the cylindrical receiving means 18a and engages behind the stop 18c of the forehead support arm 7 by rotating 90° and is held in this manner. A lateral stop point prevents a rotation of about 360° of the forehead rest 6. A vertical adjustment is made possible by a rotation by 180°. Also in this position, the forehead rest 6 is held at the forehead rest arm 7 by the undercut stop 18c at the forehead rest arm 7.

Figures 13A, 13B:
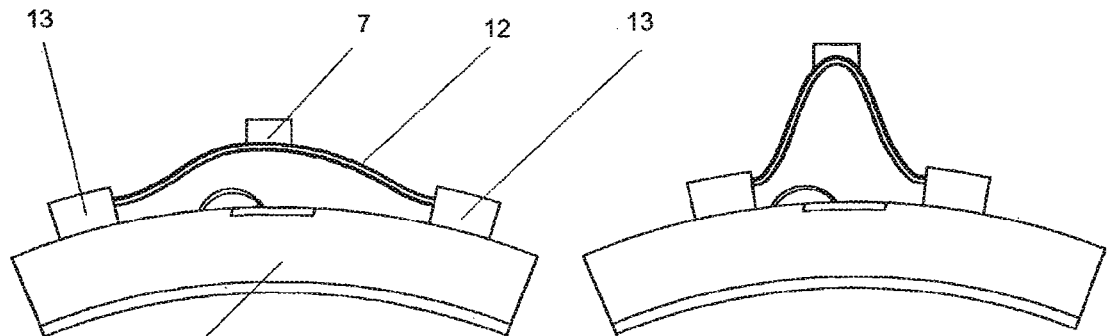
Figure 13C:
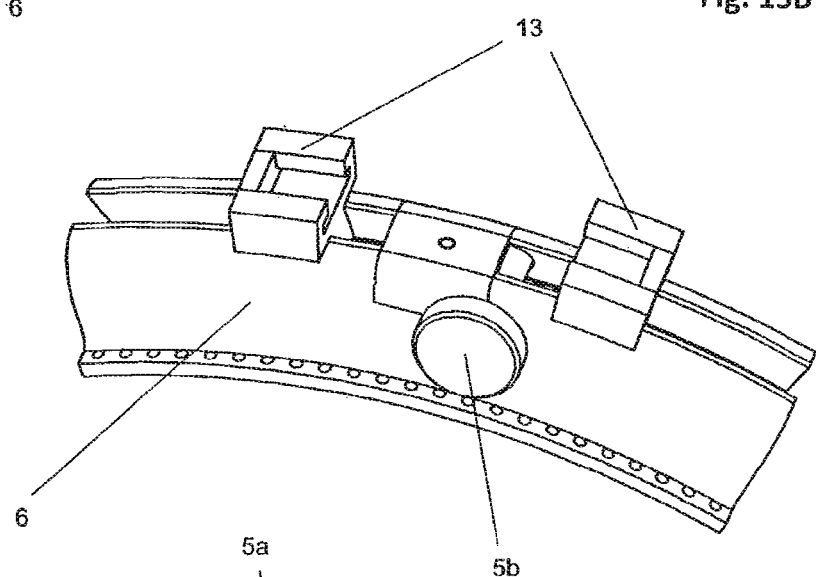
Figure 13D:
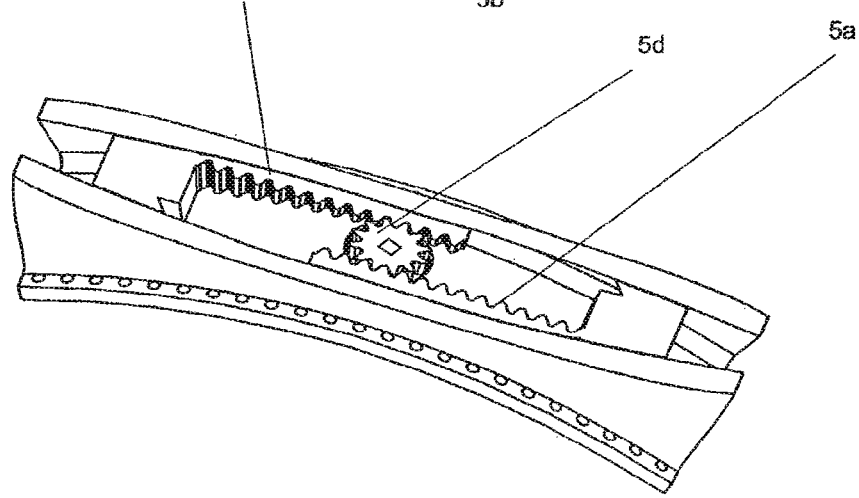

A further adjustment of the forehead rest relative to the head of the patient is realized by a deformable element 12 similar to a plate spring. Through the tension of the curve of the deformable element 12, which is arranged in the forehead rest support 6 as illustrated in FIG. 13, and is held by two lateral adjusting elements 13, the distance can be changed. Through locking slots, similar to a toothing 5a which is engaged by locking noses (teeth) of the adjusting element 5d, the deformable element 12 is moved and, in this manner, changes the distance of the forehead rest arm 7 to the face of the patient. The deformable element 12 is inserted through a slot in the forehead rest arm 7 and thereby forms a connection between the forehead rest arm 7 and the forehead rest support 6.

Figures 14A, 14B:
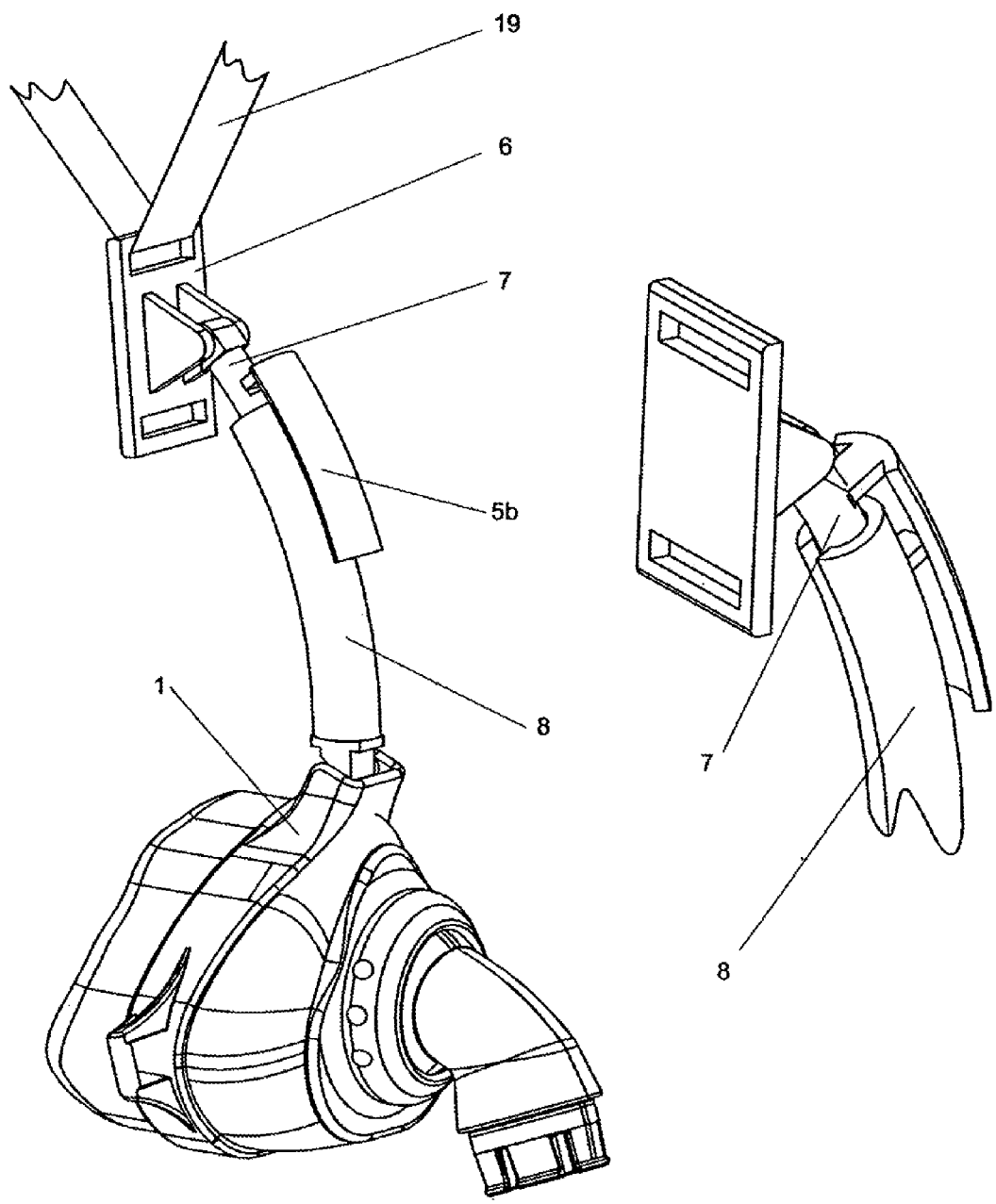

In an alternative embodiment to the constructions with a forehead support pad 6, a secure fastening of the patient interface at the head of the patient can also be effected through a support pad on the head of the patient. The overhead support pad (FIG. 14) is connected to the straps 19 and, through a curved adjusting unit 5b, 7, 8 toward the patient, to the extended shaft of the mask body 1. Thus, the patient can adjust the patient interface individually to his/her head shape. The connection of the overhead support pad 6 to the straps 19 is effected through hook and loop connections which can be easily separated and readjusted. The adjusting unit 5b, 7, 8 offers patterns of adjusting points for the optimum adjustment. Thus, the face remains completely free and it is prevented that the patient is impaired by support points in the face.

Figure 15A:
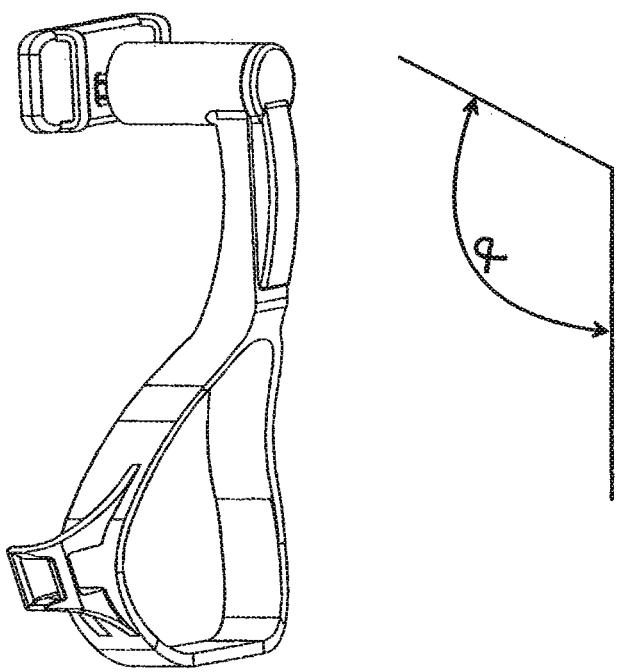
Figure 15B:
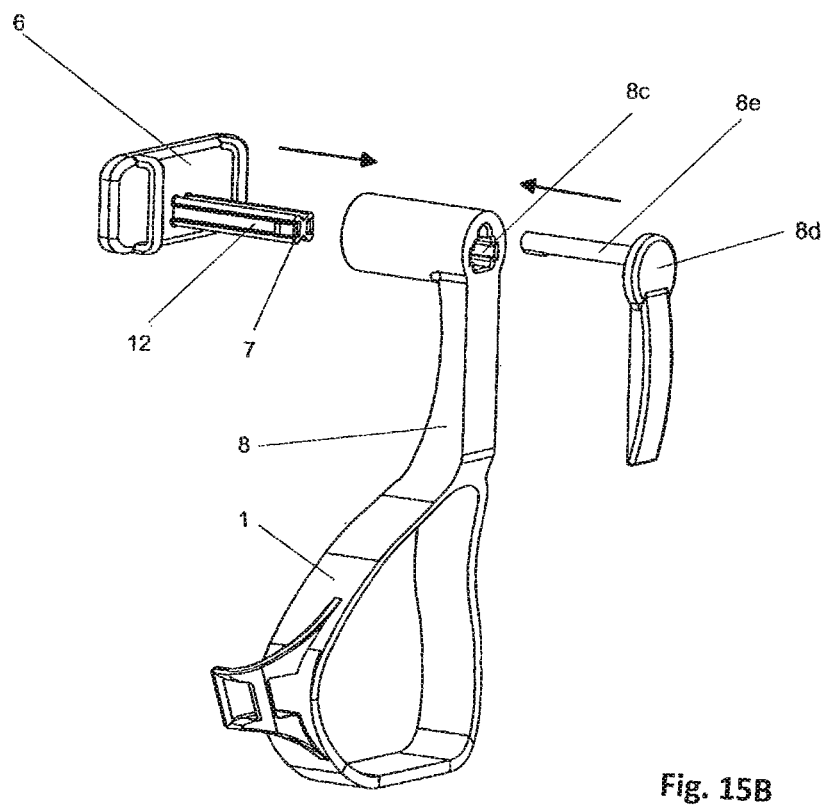

FIG. 15: A linear horizontal stepless adjustment of the forehead rest 6 is made possible by a connection in which the arm of the forehead rest support 7 is horizontally guided in a receiving means 8c of the forehead rest shaft 8. The forehead rest arm 7 has an approximately X-shaped contour and additionally has resilient elements 12 laterally in the X-shaped contour. The resilient elements 12 have a hook at the ends. The forehead rest shaft 8 is connected to the mask body 1 and has at the upper end a cylinder 8c for receiving the forehead rest arm 7. This receiving means 8c is preferably arranged horizontally, alternatively also at an angle alpha, which may be between 80° to 110°, relative to the forehead rest shaft 8 and receives on the side of the patient the arm of the forehead rest support 7 and on the opposite side a tension lever 8d. The receiving means 8c has inwardly located guide grooves complementary to the forehead rest arm 7 and the axis of the tension lever 8e, and has on the side of the patient a stop behind which the resilient elements 12 of the forehead rest arm 7 and prevent the forehead rest arm 7 from slipping out. The cylindrical axis of the tension lever 8e has at an end a thickened portion. The thickened portion serves for clamping the forehead rest arm 7 in the adjusted position. This is achieved by rotating the lever 8d into the fixed position. In the fixed position, the tension lever 8d forms a uniform silhouette with the forehead rest shaft 8. Separation is effected by turning the tension lever 8d by 90° toward the right or left. In this position of the tension lever 8d, the position of the forehead rest arm 7 can be varied steplessly.

Figure 16A:
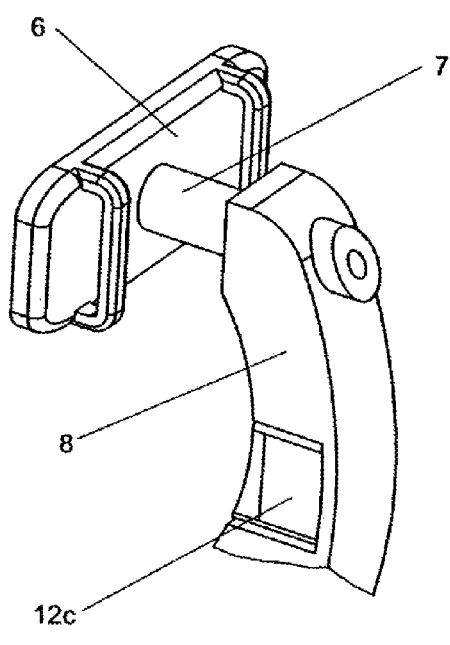
Figure 16B:
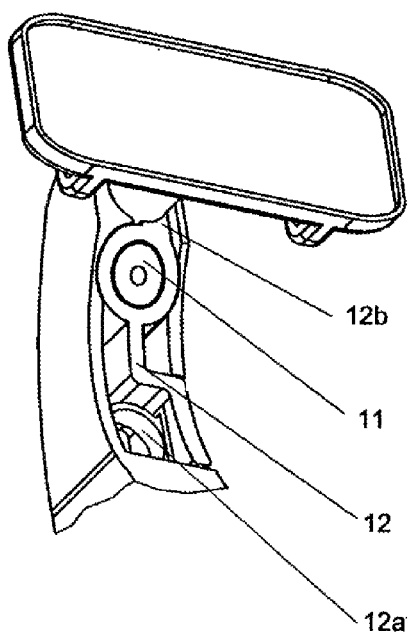

An alternative variation, in which the arm 7 of the forehead rest support 6 in the forehead rest shaft 8 is linearly horizontally displaced without steps, is illustrated in FIG. 16. The forehead rest shaft 8 is constructed so as to be open on the side of the patient and has an inwardly located tension device which clamps the arm 7 of the forehead rest support 6 in the forehead rest shaft 8 in an adjusted position. Clamping of the forehead rest arm 7 takes place through a tension lever 12 which is stored rotatably in the forehead rest shaft 8, and through the pretension a resilient element 12 in the form of a ring 12a which presses from the inside against the lower end of the tension lever 12. The tension lever 12 presses with a nose 12b mounted at an upper end against the arm 7 of the forehead rest support 6 and, thus, holds the arm 7 of the forehead rest support 6 in the desired position. For displacing the arm 7, a slight pressure applied laterally to a push button 12c on the tension lever 12 which cancels out the pretension of the resilient element 12a. The push button of the clamping lever 12c can be achieved by a lateral opening of the forehead rest shaft 8. An inclination of the forehead rest support 6 relative to the face of the patient is not necessary because a forehead cushion 6a, not shown, placed on the head makes possible a pleasant wearing comfort in any position because of its soft adaptability.

All the above are embodiments which facilitate a secure, comfortably wearable placement of the breathing device, and are simple to manipulate by the patient, and help the patient to wear the breathing device comfortably over a long period of time and to prevent the risk of a separation of the device.

The invention claimed is:

1. A breathing device, wherein the breathing device comprises a body which delimits an internal space from an external area; an area for sealing the device relative to facial areas of a patient; fastening elements for positioning the device to a head of the patient; a connection for supply of breathing gas; a forehead rest for supporting the breathing device at the head of the patient; an adjusting member which is an actuating element of the forehead rest and which, when being adjusted, is adapted to change a distance of at least one part of the device to at least one facial area of the patient, the forehead rest being movable not proportional to a movement of the adjusting member at least in portions of an adjusting range, adjustment taking place through movement of the adjusting member which engages through a stationary forehead rest shaft and includes guide elements which engage in curved guide grooves in a forehead rest support arm connected to the forehead rest and move the forehead rest support arm during the adjustment, the forehead rest support arm being slotted in a lower area thereof and having locking elements at ends of both sides thereof, which locking elements engage in corresponding openings in the forehead rest shaft.

2. The breathing device of claim 1, wherein in side view the forehead rest support arm is curved in S-shape.

3. The breathing device of claim 1, wherein transmission of movement of the adjusting member to the forehead rest takes place in a middle adjusting area of the adjusting member with a greater or smaller transmission factor than in at least one border area of the adjusting range of the adjusting member.

4. The breathing device of claim 1, wherein the device further comprises at least one of an optical, acoustic or tactile marking of an adjusted position of the forehead rest or the adjusting member.

5. The breathing device of claim 1, wherein a special adjusting position or a special adjusting area of the forehead rest is emphasized at least one of optically, acoustically or by tactile elements.

6. The breathing device of claim 1, wherein several positions or position areas in an adjusting portion of the forehead rest are emphasized at least one of optically, acoustically or by tactile elements.

7. The breathing device of claim 1, wherein the adjusting member carries out an essentially rotatory movement during adjustment.

8. A breathing device, wherein the breathing device comprises a body which delimits an internal space from an external area; an area for sealing the device relative to facial areas of a patient; fastening elements for positioning the device to a head of the patient; a connection for supply of breathing gas; a forehead rest for supporting the breathing device at the head of the patient; an adjusting member which is an actuating element of the forehead rest and which, when being adjusted, is adapted to change a distance of at least one part of the device to at least one facial area of the patient, the forehead rest being movable not proportional to a movement of the adjusting member at least in portions of an adjusting range, adjustment taking place through movement of the adjusting member which engages through a stationary forehead rest shaft and includes guide elements which engage in curved guide grooves in a forehead rest support arm connected to the forehead rest and move the forehead rest support arm during the adjustment, the forehead rest shaft and the forehead rest support arm being connected through two holding elements which are arranged on the forehead rest support arm and are rotatably supported in the forehead rest shaft.

9. The breathing device of claim 8, wherein the holding elements are pins.

10. The breathing device of claim 8, wherein in side view the forehead rest support arm is curved in S-shape.

11. The breathing device of claim 8, wherein transmission of movement of the adjusting member to the forehead rest takes place in a middle adjusting area of the adjusting member with a greater or smaller transmission factor than in at least one border area of the adjusting range of the adjusting member.

12. The breathing device of claim 8, wherein the device further comprises at least one of an optical, acoustic or tactile marking of an adjusted position of the forehead rest or the adjusting member.

13. The breathing device of claim 8, wherein a special adjusting position or a special adjusting area of the forehead rest is emphasized at least one of optically, acoustically or by tactile elements.

14. The breathing device of claim 8, wherein several positions or position areas in an adjusting portion of the forehead rest are emphasized at least one of optically, acoustically or by tactile elements.

15. The breathing device of claim 8, wherein the adjusting member carries out an essentially rotatory movement during adjustment.

* * * * *